US012703675B2

(12) United States Patent
Kim et al.

(10) Patent No.: US 12,703,675 B2
(45) **Date of Patent: *Aug. 11, 2026**

(54) METHOD FOR PREPARING ESTER-BASED COMPOSITION

(71) Applicant: LG CHEM, LTD., Seoul (KR)

(72) Inventors: Hyun Kyu Kim, Daejeon (KR); Jeong Ju Moon, Daejeon (KR); Eun Suk Kim, Daejeon (KR); Joo Ho Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 871 days.

This patent is subject to a terminal disclaimer.

(21) Appl. No.: 18/016,839

(22) PCT Filed: Sep. 17, 2021

(86) PCT No.: PCT/KR2021/012897

§ 371 (c)(1), (2) Date: Jan. 18, 2023

(87) PCT Pub. No.: WO2022/065853

PCT Pub. Date: Mar. 31, 2022

(65) Prior Publication Data

US 2023/0295071 A1 Sep. 21, 2023

(30) Foreign Application Priority Data

Sep. 24, 2020 (KR) ........................ 10-2020-0124126
Sep. 17, 2021 (KR) ........................ 10-2021-0124975

(51) Int. Cl.

*C07C 67/08* (2006.01)
*B01J 31/12* (2006.01)
*C07C 69/82* (2006.01)

(52) U.S. Cl.

CPC ............... *C07C 67/08* (2013.01); *B01J 31/12* (2013.01); *C07C 69/82* (2013.01)

(58) Field of Classification Search

None

See application file for complete search history.

(56) References Cited

U.S. PATENT DOCUMENTS 5,532,405 A 7/1996 Lyford, IV
2002/0086969 A1 7/2002 DeBruin
(Continued)

FOREIGN PATENT DOCUMENTS

CN 1291180 A 4/2001
CN 102844292 A 12/2012
(Continued)

OTHER PUBLICATIONS

Office Action dated Dec. 4, 2024 issued in corresponding to Chinese Patent Application No. 202180060415.6.
(Continued)

*Primary Examiner* — Amy C Bonaparte
(74) *Attorney, Agent, or Firm* — Morgan, Lewis & Bockius LLP

(57) ABSTRACT

The present invention relates to a method for preparing an ester-based composition, the method configured to sequentially operate a plurality of batch reactors and control pressure in each reactor, and the ester-based composition is semi-continuously prepared to have high productivity as well as stability of the batch reactors.

11 Claims, 3 Drawing Sheets

(56) References Cited

U.S. PATENT DOCUMENTS

| | | | |
|---|---|---|---|
| 2002/0091227 A1 | 7/2002 | DeBruin | |
| 2002/0137877 A1 | 9/2002 | Debruin | |
| 2004/0030175 A1 | 2/2004 | Disteldorf et al. | |
| 2009/0192285 A1 | 7/2009 | Wilhelm et al. | |
| 2010/0130767 A1* | 5/2010 | De Munck | C07C 67/08 560/99 |
| 2010/0137631 A1* | 6/2010 | De Munck | C07C 67/303 560/99 |
| 2014/0288325 A1 | 9/2014 | Yang et al. | |
| 2019/0263745 A1 | 8/2019 | Lee et al. | |
| 2020/0317600 A1* | 10/2020 | Kim | B01J 19/0053 |

FOREIGN PATENT DOCUMENTS

| | | |
|---|---|---|
| JP | 2002-155026 A | 5/2002 |
| JP | 3415723 B2 | 6/2003 |
| JP | 2010-520944 A | 6/2010 |
| JP | 2013-525325 A | 6/2013 |
| KR | 10-2003-0048469 A | 6/2003 |
| KR | 10-2003-0068171 A | 8/2003 |
| KR | 10-1354141 B1 | 1/2014 |
| KR | 10-2014-0077342 A | 6/2014 |
| KR | 10-2014-0115977 A | 10/2014 |
| KR | 10-1663586 B1 | 10/2016 |
| KR | 10-2019-0027623 A | 3/2019 |
| WO | 99/41226 A1 | 8/1999 |
| WO | 2005/082970 A1 | 9/2005 |

OTHER PUBLICATIONS

Rahman et al., “The plasticizer market: an assessment of traditional plasticizers and research trends to meet new challenges,” Progress in Polymer Science, 29: 1223-1248 (2004).

Janjua et al., “Systemic Uptake of Diethyl Phthalate, Dibutyl Phthalate, and Butyl Paraben Following Whole-Body Topical Application and Reproductive and Thyroid Hormone Levels in Humans,” Environmental Science and Technology, 41: 5564-5570 (2007).

International Search Report (with partial translation) and Written Opinion dated Jan. 10, 2022, for corresponding International Patent Application No. PCT/KR2021/012897.

Office Action issued corresponding Japanese Patent Application No. 2023-501851 dated Dec. 25, 2023.

Extended European Search Report issued in corresponding European Patent Application No. 21872881.4 dated Mar. 6, 2024.

Office Action issued on May 25, 2024 in corresponding Chinese Patent Application 202180060415.6.

* cited by examiner

METHOD FOR PREPARING ESTER-BASED COMPOSITION

CROSS-REFERENCE TO RELATED APPLICATIONS

This application claims the benefit of Korean Patent Application Nos. 10-2020-0124125, filed on Sep. 24, 2020, and 10-2021-0124974, filed on Sep. 17, 2021, in the Korean Intellectual Property Office, the disclosures of which is are incorporated herein in its entirety their entireties by reference.

TECHNICAL FIELD

The present invention relates to a method for preparing an ester-based composition, the method configured to sequentially operate a plurality of batch reactors and control pressure in each reactor.

BACKGROUND ART

Phthalate-based plasticizers had accounted for 92% of the global plasticizer market by the 20th century (see Mustafizur Rahman and Christopher S. Brazel, "The plasticizer market: an assessment of traditional plasticizers and research trends to meet new challenges", Progress in Polymer Science 2004, 29, 1223-1248), and are additives used for imparting flexibility, durability, and cold resistance mainly to polyvinyl chloride (hereinafter referred to as PVC) and lowering the viscosity during melting to improve processability. These phthalate-based plasticizers are added in various amounts to PVC and widely used in various applications from rigid products such as rigid pipes to soft products which may be used for such as food packaging materials, blood bags, flooring materials, etc. due to their soft and good flexibility, and thus are more closely related to real life than any other material, and the direct contact with the human body may not avoidable.

However, despite the compatibility of the phthalate-based plasticizers with PVC and their excellent capability to impart flexibility, it has been argued recently about harmfulness of the PVC product containing the phthalate-based plasticizers that the phthalate-based plasticizers may leak out of the PVC product when used in real life, and act as a presumed endocrine disrupting (environmental hormone) substance and a carcinogen of the level of heavy metals (see N. R. Janjua et al., "Systemic Uptake of Diethyl Phthalate, Dibutyl Phthalate, and Butyl Paraben Following Whole-body Topical Application and Reproductive and Thyroid Hormone Levels in Humans", Environmental Science and Technology 2007, 41, 5564-5570). Especially, since the report about the leakage of di-(2-ethyl hexyl) phthalate (DEHP), which was the most used phthalate-based plasticizer in the US in the 1960s, out of the PVC product, the interest in environmental hormones has been added in the 1990s and global environmental regulations as well as extensive studies on hazards of the phthalate-based plasticizers to human have started.

Therefore, in order to cope with environmental hormone problems and environmental regulations due to the leakage of the phthalate-based plasticizers, a number of researchers have been conducting research to develop a new, alternative, non-phthalate-based plasticizer which is free of phthalic anhydride used in the production of phthalate-based plasticizers or a leakage inhibition technology which may inhibit the leakage of the phthalate-based plasticizers to greatly reduce the hazards to human and be in accordance with environmental standards.

Meanwhile, as a non-phthalate-based plasticizer, a terephthalate-based plasticizer has been getting the spotlight, because it is equivalent to the phthalate-based plasticizer in terms of physical properties, but is free of environmental issues. A variety of terephthalate-based plasticizers have been developed and researched on the development of a terephthalate-based plasticizer having excellent physical properties, as well as researched on facilities for preparing such the terephthalate-based plasticizer have been actively conducted. In terms of process design, more efficient, economical, and simple process design has been required.

RELATED ART DOCUMENT (Patent Document 1) Korean Patent Laid-Open Publication No. 10-1354141

(Non-patent Document 1) Mustafizur Rahman and Christopher S. Brazel "The plasticizer market: an assessment of traditional plasticizers and research trends to meet new challenges" Progress in Polymer Science 2004, 29, 1223-1248

(Non-patent Document 2) N. R. Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2007, 41, 5564-5570

DISCLOSURE OF THE INVENTION

Technical Problem

The present invention is to provide an efficient method for preparing an ester-based composition, the method employing a plurality of batch reactors mainly used for an esterification reaction, connecting the reactors in parallel, and sequentially operating the reactors to ensure that the entire process is semi-continuously operated and pressure in each reactor is controlled, thereby achieving both the stability of the batch reactors themselves and the efficiency of the semi-continuous process.

Technical Solution

To solve the tasks, the present invention provides a method for preparing an ester-based composition.

(1) There is provided a method for preparing an ester-based composition, the method comprising: putting a polycarboxylic acid and a mono-alcohol having 3 to 12 alkyl carbon atoms into a mixer to form a reaction mixture (S1); sequentially putting the reaction mixture into N batch reactors connected in parallel perform a reaction, and sequentially completing the reaction in the N batch reactors to semi-continuously produce reaction products (S2); and semi-continuously moving the reaction products to a separation unit to remove unreacted alcohol (S3), wherein N above is an integer of 3 or more, pressures of the N reactors are each independently configured such that the pressure at the early stage is 0.3 barg to 1.0 barg and the pressure at the latter stage is 0 barg to 0.5 barg, the pressure at the early stage being greater than the pressure at the latter stage, and the early and latter stages are divided based on any one of the time points when reaction conversion rate is 30% to 90%.

(2) The present invention provides the method according to (1) above, wherein the batch reactors have an early stage pressure of 0.4 barg to 1.0 barg, and a latter stage pressure of 0 barg to 0.4 barg.

(3) The present invention provides the method according to (1) or (2) above, wherein the mono-alcohol is added in excess of 20 mol % to 100 mol % relative to polycarboxylic acid equivalent.

(4) The present invention provides the method according to any one of (1) to (3) above, wherein the latter stage pressure gradually decreases as reactions proceed.

(5) The present invention provides the method according to any one of (1) to (4) above, wherein the method further includes additionally inputting the mono-alcohol in the course of reactions (Sa).

(6) The present invention provides the method according to any one of (1) to (5) above, wherein the method further includes at least one step selected from the group consisting of: adding a catalyst to the reaction mixture between the step S1 and the step S2 (S1-1), adding a catalyst to a polycarboxylic acid and mono-alcohol before the step S1 (S1-2), and adding a catalyst to each of the N batch reactors of the step S2 (S2a).

(7) The present invention provides the method according to any one of (1) to (6) above, wherein the catalyst is tetraalkyl titanate.

(8) The present invention provides the method according to any one of (1) to (7) above, wherein the step S1 further comprises heating the reaction mixture to 50 to 200° C.

(9) The present invention provides the method according to any one of (1) to (8) above, wherein the reaction of the step S2 is performed at 130 to 250° C.

(10) The present invention provides the method according to any one of (1) to (9) above, wherein the polycarboxylic acid is at least one selected from the group consisting of a dicarboxylic acid, a tricarboxylic acid, and a tetracarboxylic acid.

(11) The present invention provides the method according to any one of (1) to (10) above, wherein: the dicarboxylic acid is at least one selected from the group consisting of a linear dicarboxylic acid having 2 to 10 carbon atoms, a terephthalic acid, a phthalic anhydride, an isophthalic acid, a cyclohexane dicarboxylic acid, an anhydride thereof, and a derivative thereof; the tricarboxylic acid is at least one selected from the group consisting of a citric acid, a trimellitate acid, a cyclohexane tricarboxylic acid, an anhydride thereof, and a derivative thereof; and the tetracarboxylic acid is at least one selected from the group consisting of a benzenetetracarboxylic acid, a furantetracarboxylic acid, a cyclohexane tetracarboxylic acid, a tetrahydrofuran tetracarboxylic acid, an anhydride thereof, and a derivative thereof.

Advantageous Effects

A preparation method of the present invention is configured to sequentially operate a plurality of batch reactors connected in parallel to ensure that an entire reaction process is semi-continuously operated and pressure in each reactor is controlled, and thus, an ester-based composition may be efficiently and stably prepared.

MODE FOR CARRYING OUT THE INVENTION

Figure 1:
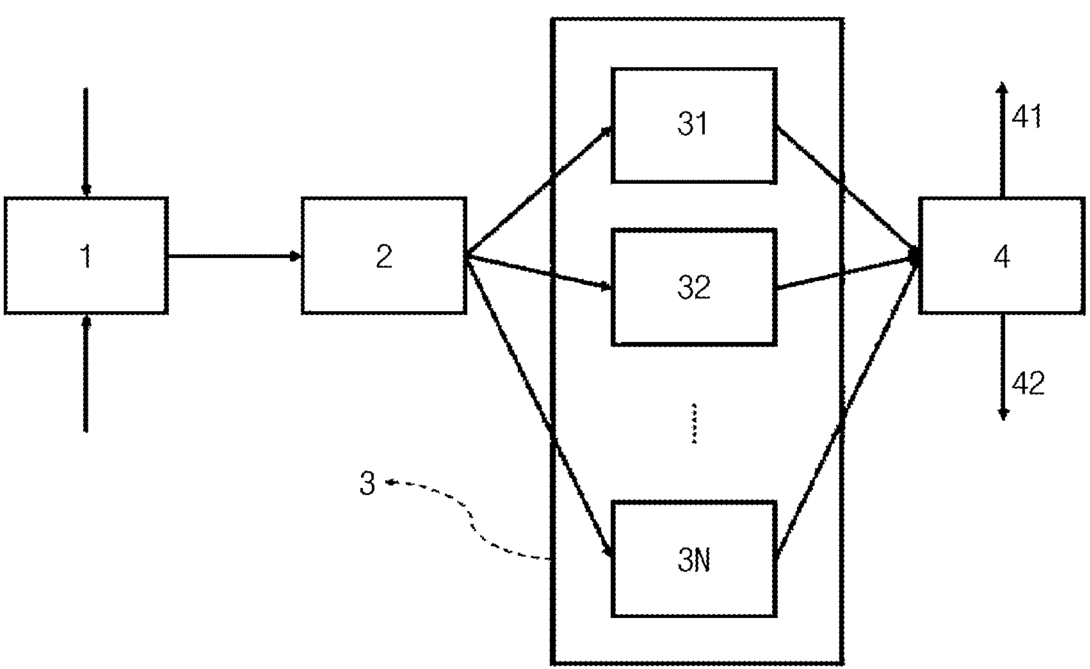
FIG. 1 is a process flowchart illustrating a system for preparing an ester-based composition including a mixer, a supply controller, a reaction unit, and a separation unit according to an embodiment of the present invention.

Hereinafter, the present invention will be described in more detail.

It will be understood that words or terms used in the specification and claims of the present invention shall not be construed as being limited to having the meaning defined in commonly used dictionaries. It will be further understood that the words or terms should be interpreted as having meanings that are consistent with their meanings in the context of the relevant art and the technical idea of the invention, based on the principle that an inventor may properly define the meaning of the words or terms to best explain the invention.

In the preparation method of the present invention, a polycarboxylic acid refers to a compound having two or more carboxylic acid groups, and may indicate, for example, a dicarboxylic acid, a tricarboxylic acid, or a tetracarboxylic acid. A polycarboxylic acid used in the present invention may have 2 to 5 carboxylic acid groups, 2 to 4 carboxylic acid groups, or 2 to 3 carboxylic acid groups. When a polycarboxylic acid has too many carboxylic acid groups, the polycarboxylic acid may not be well applied to the preparation method or a preparation system of the present invention due to a high molecular weight of the polycarboxylic acid itself. The polycarboxylic acid is preferably a dicarboxylic acid, a tricarboxylic acid, or a tetracarboxylic acid particularly, and the dicarboxylic acid may be at least one selected from the group consisting of a linear dicarboxylic acid having 2 to carbon atoms, a terephthalic acid, a phthalic anhydride, an isophthalic acid, and a cyclohexane dicarboxylic acid, the tricarboxylic acid may be at least one selected from the group consisting of a citric acid, a trimellitate acid, and a cyclohexane tricarboxylic acid, and the tetracarboxylic acid may be at least one selected from the group consisting of a benzenetetracarboxylic acid, a furantetracarboxylic acid, a cyclohexane tetracarboxylic acid, and a tetrahydrofuran tetracarboxylic acid. In addition, the polycarboxylic acid may not only include itself, but also include an anhydride or a derivative thereof.

In the preparation method of the present invention, mono-alcohol having 3 to 12 alkyl carbon atoms may be preferably at least one selected from the group consisting of propanol, butanol, pentanol, hexanol, heptanol, octanol, nonanol, decanol, undecanol, and dodecanol, all of which are of a linear type or a branched type, and more preferably, may be mono-alcohol having 4 to 10 carbon atoms. In addition, the alcohol may be a single type of alcohol, or may be in the form of a mixture containing isomers having the same number of carbon atoms. For example, when the alcohol is alcohol having 3 alkyl carbon atoms, the alcohol may be 1-propanol or 2-propanol, or may be in the form of a mixture containing 1-propanol and 2-propanol in a certain ratio. When the alcohol is in the form of a mixture containing isomers having the same number of carbon atoms, the relative amount of each isomer is not particularly limited.

Ester-Based Composition Preparation System

First, a preparation system for carrying out a preparation method of the present invention will be described. Specifically, the method for preparing an ester-based composition of the present invention may be carried out through a system for preparing an ester-based composition, the system including: a mixer in which a reaction mixture of a polycarboxylic acid and (at least one) alcohol having 3 to 12 alkyl carbon atoms is formed; N batch reactors connected in parallel in which an esterification reaction of the reaction mixture is performed; an inlet line for receiving the reaction mixture from the mixer; a reaction unit provided with an outlet line discharging reaction products from the N batch reactors; a supply controller for controlling the input amount and input path of the reaction mixture such that the reaction mixture is sequentially supplied to the N batch reactors from the mixer to sequentially complete reactions; and a separation unit for receiving the reaction products through the outlet line of the reaction unit to remove unreacted alcohol.

The preparation system in which the method for preparing an ester-based composition of the present invention is carried out includes a mixer 1, a supply controller 2, a reaction unit 3, and a separation unit 4.

As shown in FIG. 1, the mixer 1 performs mixing of a polycarboxylic acid 11 and an alcohol 12 that are put into the mixer, and a reaction mixture generated from the mixer is sequentially put into each batch reactor 31 to 3N included in the reaction unit 3 through the supply controller 2. When the reaction in each reactor is completed, the reaction products move to the separation unit 4 where unreacted alcohol 42 is removed, and an ester-based composition 41 is finally obtained.

In particular, the supply controller 2 included in the preparation system of the present invention serves a role of determining input start time, input amount, and input completion time for each reactor when sequentially putting the reaction mixture into each reactor from the mixer, thereby enabling the sequential input of the reaction mixture to each reactor connected in parallel and the discharge of reaction products.

Figure 2:
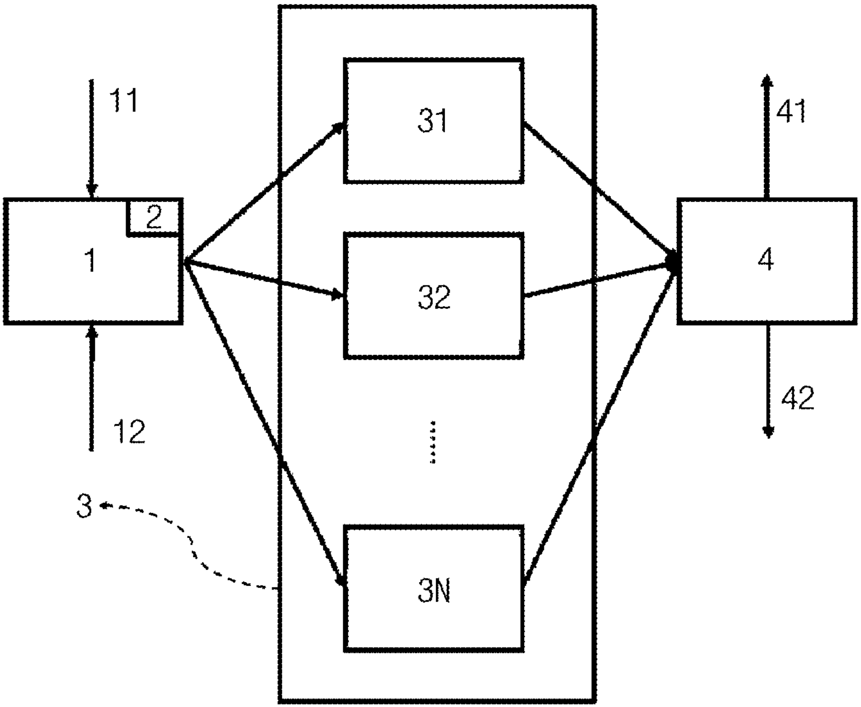
FIG. 2 is a process flowchart illustrating a system for preparing an ester-based composition including a mixer, a supply controller, a reaction unit, and a separation unit, wherein the supply controller is provided inside the mixer according to an embodiment of the present invention.

The supply controller may be a separate unit connected to the mixer as shown in FIG. 1 or may be a unit included in the mixer as shown in FIG. 2. When the supply controller is included in the mixer, the supply controller may control the input path and the input amount of the reaction mixture directly discharged from the mixer.

Figure 3:
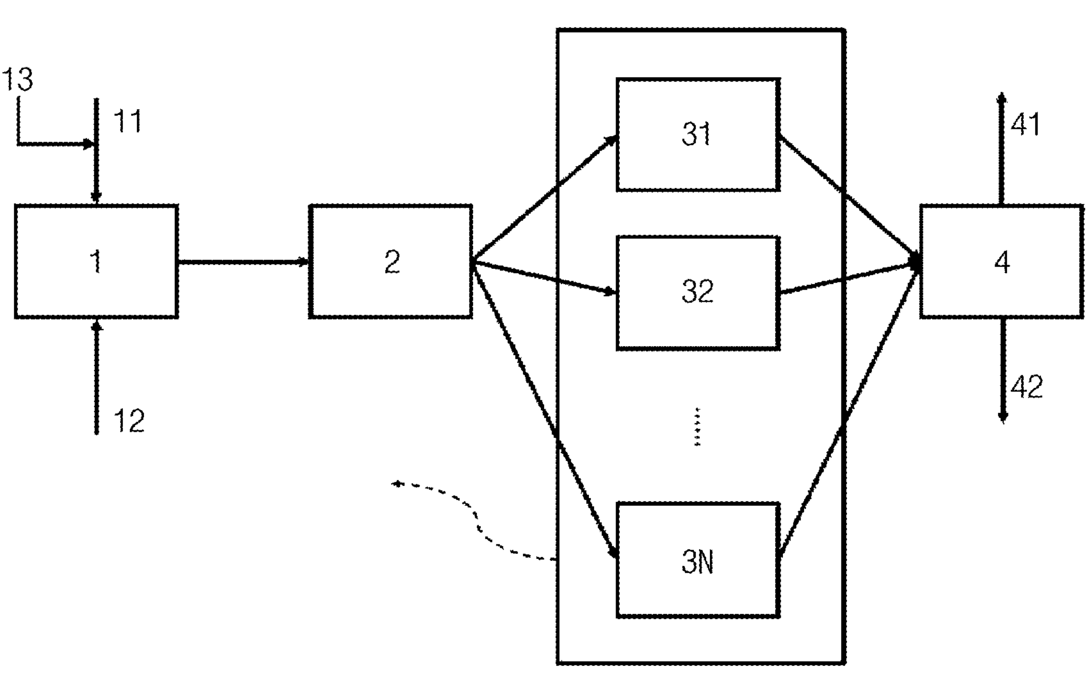
FIGS. 3 to 5 are process flowcharts illustrating a system for preparing an ester-based composition in which each path through which a catalyst may be input is indicated in an embodiment of the present invention.
Figure 4:
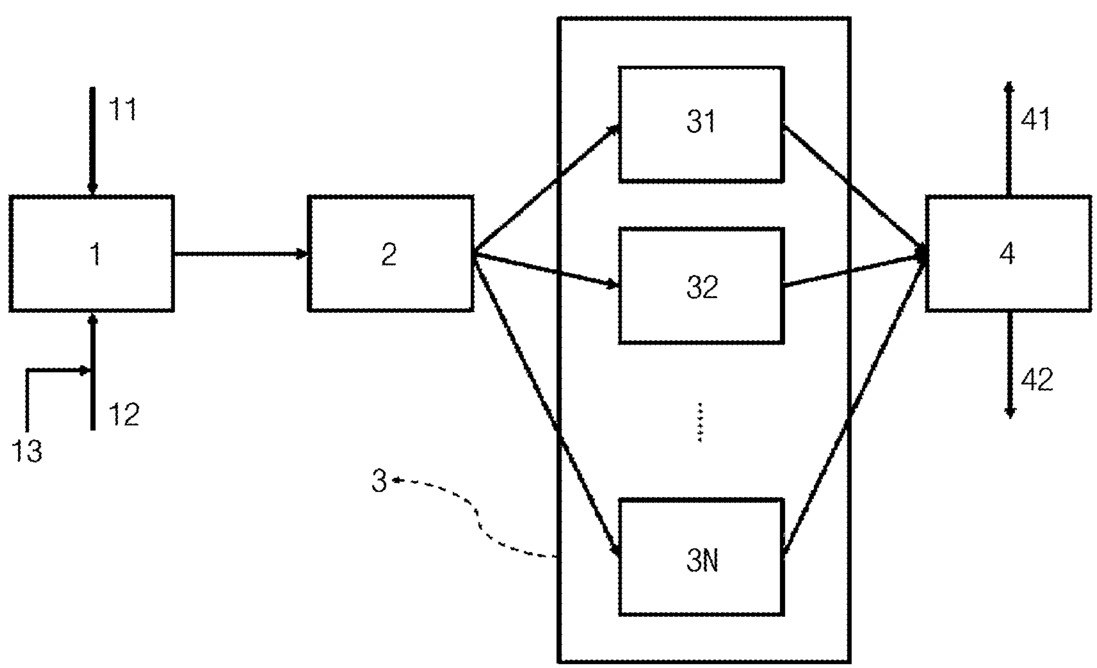
Figure 5:
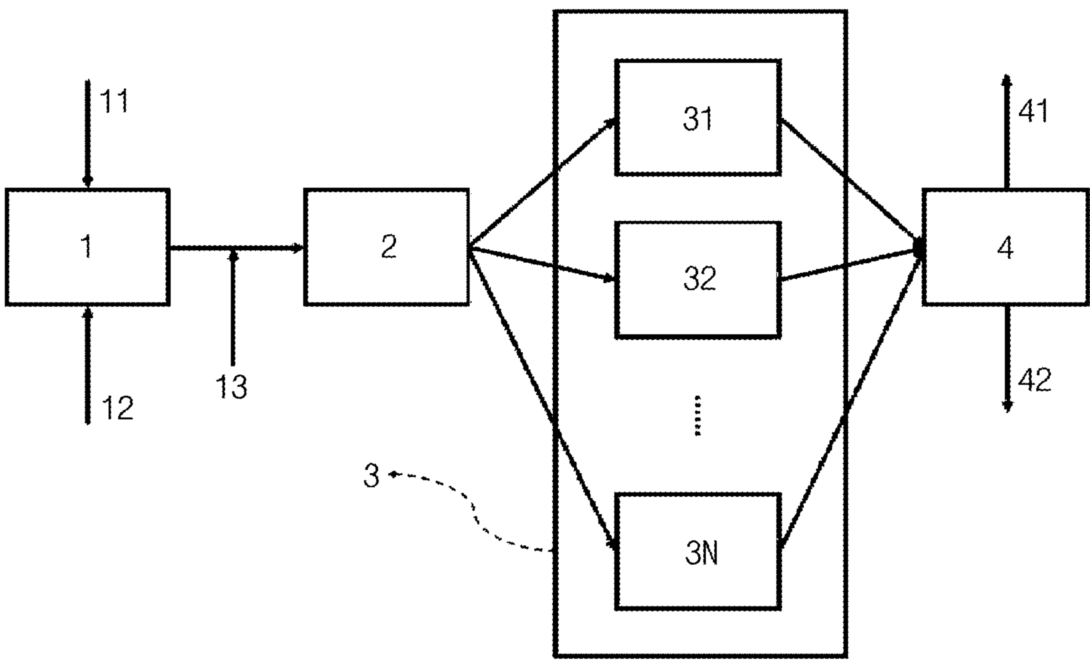

In addition, as shown in FIG. 3, 4, or 5, the preparation system of the present invention may add the catalyst 13 to a polycarboxylic acid, an alcohol, or a reaction mixture thereof.

Figure 6:
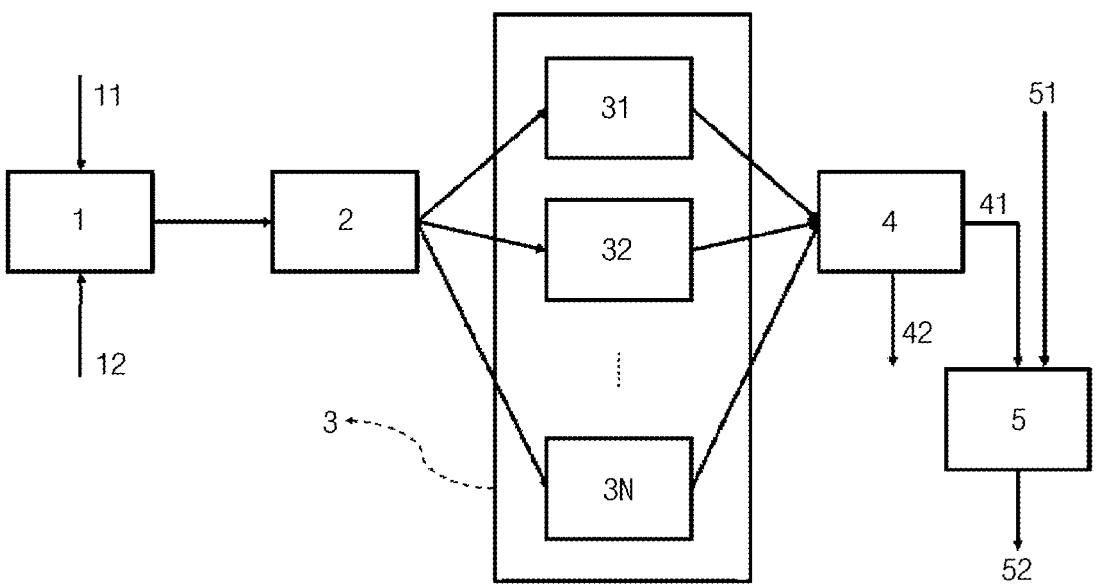
FIG. 6 is a process flowchart illustrating a system for preparing an ester-based composition including a mixer, a supply controller, a reaction unit, a separation unit, and a trans reaction unit according to an embodiment of the present invention.

As shown in FIG. 6, the preparation system provided by the present invention may further include a trans reaction unit 5 for adding an alcohol having 3 to 12 alkyl carbon atoms to reaction products from which unreacted alcohol is removed to perform a trans-esterification reaction. The alcohol 52 input from the trans reaction unit is different from the alcohol input from the mixer, and the ester-based composition 51 including different ester-based compounds may be prepared through the trans reaction unit.

In addition, in the preparation system provided by the present invention may be provided with a gas-liquid separation column in which at least one of the N reactors is connected to an upper portion of the reactor, and alcohol and water discharged through the upper portion of the reactor are separated, a condenser for cooling gas discharged through an upper line of the gas-liquid separation column, and a decanter for separating liquid discharged through a lower line of the gas-liquid separation column and liquid condensed in the condenser into different layers and recirculating the alcohol into the reactor.

As described above, when a reactor is provided with a gas-liquid separation column, a condenser, and a decanter, it is possible to increase the efficiency and economic feasibility of the reaction by re-liquefying alcohol vaporized during the reaction and putting the re-liquefied alcohol back into the reactor, and at the same time, it is possible to allow the reaction to proceed towards a forward reaction by removing water, which is a by-product of an esterification reaction, that is, allowing a high conversion rate to be achieved.

In addition, the supply controller in the preparation system provided by the present invention may control such that at least one selected from the input path and the input flow of the reaction mixture according to a set time interval is altered.

The supply controller in the preparation system of the present invention needs to determine the input path and the input flow of the reaction mixture such that N reactors may work sequentially, and accordingly, when a determined time interval is set considering the reaction time, the total number of reactors, and the desired production volume, and the input path and the input flow of the reaction mixture is controlled at the time interval described above, after the reaction is completed in each reactor, the reaction mixture starts to be put back into a corresponding reactor at the time when reaction products are all or almost discharged, so that all of the reactors may be operated without being stopped, and the efficiency of the process may be increased.

In addition, the time interval set in the supply controller may be 50%, 60%, 70%, 80%, or 90% or more, and may be 150%, 140%, 130%, 120%, or 110% or less of the value obtained by dividing the reaction time in one reactor by N. When the time interval is set in the ranges described above, the loss of reactor operation failure may be minimized.

Meanwhile, the above-described reaction duration is a sum of the amount of time consumed for the reaction and the amount of time consumed for the input of the reaction mixture and the discharge of the reaction products. For example, when 30 minutes are consumed for the reaction, and 15 minutes are consumed for each of the input of the reaction mixture and the discharge of the reaction products, the reaction duration is 60 minutes. In this case, when there are four reactors, the input time interval for each reactor is 15 minutes, so that the input of the reaction mixture for each reactor starts every 15 minutes.

Method for Preparing Ester-Based Composition

The present invention provides a method for preparing an ester-based composition, the method including: putting a polycarboxylic acid and a mono-alcohol having 3 to 12 alkyl carbon atoms into a mixer to form a reaction mixture (S1); sequentially putting the reaction mixture into N batch reactors connected in parallel to perform a reaction, and sequentially completing the reaction in the N batch reactors to semi-continuously produce reaction products (S2); and semi-continuously moving the reaction products to a separation unit to remove unreacted alcohol (S3), wherein N above is an integer of 3 or more.

In addition, in the method for preparing an ester-based composition of the present invention, pressures of the N reactors are each independently configured such that the pressure at the early stage is 0.3 barg to 1.0 barg and the pressure at the latter stage is 0 barg to 0.5 barg, the pressure at the early stage being greater than the pressure at the latter stage, and the early and latter stages are divided based on any one of the time points when reaction conversion rate is 30% to 90%.

In the present description, the early stage of reaction may refer to any one of the time points between 30% to 90%, preferably 30% to 80%, 40% to 80%, or 50% to 80% of the conversion rate from the time when temperature starts to rise after reactants are put into a reactor, whereas the latter stage of reaction may refer to the time from the one time point defined above to the time point at which the reaction is completed. In this case, the completion of the reaction may indicate that the residual amount of materials used as limited reactants out of polycarboxylic acid and mono-alcohol of reactants falls to a level of 1% or less with respect to the input amount, or the conversion rate of the reaction is at least 97% or more, preferably, 98% or more, or 99% or more. This considers that the reactants may be arbitrarily processed according to conditions through chemical engineering methods such as pressure reduction, pressurization, distillation, extraction, filtration, and the like depending on apparatuses and equipment conditions, and efficiency and product quality may be guaranteed only when processes are designed to make sure that reaction conversion rate reaches a level of 99% or more.

Mixing Step (S1)

The preparation method of the present invention includes putting a polycarboxylic acid and at least one alcohol having 3 to 12 alkyl carbon atoms into a mixer to form a reaction mixture (S1).

Specifically, the step S1 of forming the reaction mixture refers to a step of uniformly mixing the polycarboxylic acid and at least one alcohol having 3 to 12 alkyl carbon atoms in a mixer. In the present step, before the polycarboxylic acid and the alcohol having 3 to 12 carbon atoms, which correspond to reaction raw materials, are put into a reactor, the polycarboxylic acid and the alcohol having 3 to 12 carbon atoms are uniformly pre-mixed in the mixer, so that it is possible to prevent non-uniform reaction which may occur when the raw materials are directly put into the reactor. In particular, since the reactor used in the present invention is a batch reactor, when reaction raw materials are not pre-mixed before being putting into a reactor, depending on the position inside the reactor, the non-uniformity of the raw materials may be greatly increased, and when stirring is poorly performed inside the reactor, some raw materials may be accumulated in particular, and thus, it may be difficult to secure uniform reaction duration and conversion rate. However, when reaction raw materials are pre-mixed and then input, it is possible to obtain a substantially uniform reaction degree over the entire region of the reactor, and the reaction rate of each reactor may be maintained to be substantially uniform to secure the stability of the entire process.

In the preparation method of the present invention, the step S1 may further include a step in which the reaction mixture is heated to 50 to 200° C., preferably 60 to 190° C., more preferably 70 to 180° C. Since the reaction mixture is heated in the step S2 after step S1 to perform the reaction, when the reaction mixture is pre-heated and put into a reactor in the step S1, the reaction mixture may react easily and quickly in the reactor. However, when an elevated temperature in the step S1 is too low, the effect of pre-heating before the input is poor, and when the reaction mixture is heated to an excessively high temperature and put into a reactor, the polycarboxylic acid and the mono-alcohol having 3 to 12 alkyl carbon atoms, which are reaction raw materials, may be vaporized, or the like, so that a uniform reaction may not rather proceed.

Reaction Step (S2)

The method for preparing an ester-based composition of the present invention includes sequentially putting the reaction mixture into N batch reactors connected in parallel to perform a reaction, and sequentially completing the reaction in the N batch reactors to semi-continuously produce reaction products (S2).

In the case of a reaction process using a typical batch reactor, although a large amount of reaction products could be stably produced at one time, a reactor is not operated during a process in which reaction raw materials are input or the reaction products are discharged, so that there is a disadvantage in terms of the efficiency of the entire process. Therefore, the inventor of the present invention has come up with a method for preparing an ester-based composition, the method allowing a plurality of batch reactors to be used sequentially to maintain the stability of a batch reactor and to semi-continuously produce reaction products.

Specifically, in the step S2 in the preparation method of the present invention, the reaction mixture is sequentially put into the N reactors, each batch reactor into which the reaction mixture is put is heated to complete a reaction, and each batch reactor in which the reaction is completed also sequentially discharges reaction products.

For example, the step S2 may be performed in the following manner:

1) A reaction mixture uniformly mixed in a mixer is put into a first reactor, and after a predetermined amount of the reaction mixture is put into the first reactor, the input is stopped.
2) After the input is stopped, the first reactor is heated to perform a reaction, and the mixer puts the reaction mixture into a second reactor.
3) After a predetermined amount of the reaction mixture is put into the second reactor, the input is stopped. After this point, the second reactor is heated to perform a reaction, and the mixer puts the reaction mixture into a third reactor.
4) N reactors sequentially produce reaction products in the above manner, and after the reaction mixture is put into an N-th reactor, the reaction mixture is put back into the first reactor. In addition, reaction products produced after the reaction is completed are sequentially discharged in the same manner.

In the step S2, time interval between input for each reactor, that is, the time interval upon sequential input may be 90% to 110%, preferably 100% of a value obtained by dividing the total duration of reaction by N reactors. When the reaction mixture is put into each reactor at the time interval described above, after the reaction is completed in each reactor, the reaction mixture begins to be put back into a corresponding reactor at the time when reaction products are all or almost discharged, so that all of the reactors may be operated without being stopped, and the efficiency of the process may be increased.

The above-described reaction duration is a sum of the amount of time consumed for the reaction and the amount of time consumed for the input of the reaction mixture and the discharge of the reaction products. For example, when 30 minutes are consumed for the reaction, and 15 minutes are consumed for each of the input of the reaction mixture and the discharge of the reaction products, the reaction duration is 60 minutes. In this case, when there are four reactors, the input time interval for each reactor is 15 minutes, so that the input of the reaction mixture for each reactor starts every 15 minutes.

In the preparation method of the present invention, pressure of each of the N reactors in which the step S2 is performed is controlled during the reaction.

Specifically, each of the N reactors has an early stage pressure of 0.3 barg to 1.0 barg, and a latter stage pressure of 0 barg to 0.5 barg. In this case, pressure barg is a gauge pressure of a reactor without taking absolute pressure into account, and 0 barg may indicate a pressure equal to atmospheric pressure.

In the preparation method according to an embodiment of the present invention, the reaction temperature at which an esterification reaction is performed is a temperature equal to or above the boiling point of mono-alcohol, and as the reaction proceeds, a portion of the mono-alcohol is not involved in the reaction and thus is vaporized, and at the same time, water is generated as a reaction by-product and the water forms an azeotropic state with the mono-alcohol and is refluxed to an upper portion of the reactor. Such a reflux process is inevitable upon the esterification reaction, and how the reflux process is controlled may greatly affect reaction productivity and energy efficiency.

In such reaction conditions, when an esterification reaction is performed under pressure by increasing the pressure at the early stage of reaction, the vaporized alcohol may be retained at the site where the reaction takes place in the reactor to some extent, thereby leading to accelerated reaction rate and reduced reflux amount to increase energy efficiency.

As in the present invention, when the reaction is performed under pressure by increasing the pressure at the early stage as the pressure of the reactor is set to 0.3 barg to 1.0 barg, the vaporization of alcohol occurring at the beginning of reaction is suppressed as much as possible and the amount of water present in the reactor is small at the early stage of reaction, and thus the issues described above are hardly seen.

However, when the pressure is set to less than 0.3 barg, the reflux of mono-alcohol is hardly suppressed, and thus a significant amount of alcohol is vaporized and refluxed, and this causes a great deal of energy use while a condenser and a bed separator are circulated from the reactor, and further due to such a reflux circulation, an absolute amount of alcohol required to be present and involved in the reaction is lost to deteriorate reactivity, and an additional input of alcohol to make up for the loss may cause an additional loss of energy, resulting in a continuous vicious cycle.

In addition, when the pressure is set to greater than 1.0 barg, reflux is suppressed as much as possible and the amount of alcohol present in the reactor increases, but at the same time, water generated as a reaction product also increases, thereby inducing a reverse reaction to reach a reversible reaction state at a certain level, causing a significant reduction in forward reaction rate. To prevent the above issues and increase reaction rate and energy efficiency, the pressure at the early stage of reaction may be controlled preferably to be 0.3 barg to 1.0 barg, preferably 0.4 to 1.0 barg, more preferably 0.5 to 0.9 barg, or 0.5 to 0.8 barg.

Meanwhile, the reaction under pressure as described above needs to be released at an appropriate time point. When the reaction is performed only under pressure upon the reaction process, water, a by-product of the reaction stays longer in the reactor, and when the water is not removed, the reaction may not be performed well in the forward reaction direction, resulting in reduced reaction rate. In addition, a catalyst is sensitive to water, and thus the catalyst may be deactivated. As such, the reaction pressure control in the esterification reaction does not solely bring about reaction improvement, but results in both improvement and deterioration together.

Accordingly, the time to release pressure may be selected in terms of preventing catalyst deactivation or reverse reaction activation caused by the presence of water, and reduced reaction rate due to an increase in the reflux amount of alcohol, and accordingly, the time point needs to be after at least 30% of the reaction conversion, and needs to be set at a level of no greater than 90% at most. That is, the early stage of reaction and latter stage of reaction are divided at the time between 30% to 90% of reaction conversion, preferably between 30% to 80%, more preferably between 40% to 80%, or between 50% to 80%. When the pressure of the reactor is lowered to an appropriate level at the time of such conversion rate, there is an advantage in that both energy saving and productivity improvement may be achieved.

The reactor pressure at the latter stage of reaction after this point is set down to 0 barg to 0.5 barg. In this case, the pressure at the latter stage of reaction needs to be less than the pressure at the early stage of reaction, and may preferably be 0 barg to 0.4 barg. The reactor pressure at the latter stage of reaction is set to be at least atmospheric pressure or higher, but it may be meaningful to be lower than the pressure at the early stage of reaction. As such, when the pressure is released at the latter stage of reaction, it may be effective to remove a certain amount of generated water, and due to the input of an excess amount of mono-alcohol, the amount of mono-alcohol remaining in the reactor may be higher than the equivalent even when a certain portion thereof is refluxed, and thus, the removal of water may make a more significant contribution. In addition, as a catalyst serves a more important role towards the latter stage of reaction, preventing deactivation of the catalyst while continuously removing water may also be critical.

Meanwhile, in addition, the pressure at the latter stage may be controlled to gradually decrease as the reaction proceeds. For example, after the pressure is reduced from the pressure at the early stage to the pressure at the latter stage, as the reaction proceeds, the pressure at the latter stage may be controlled to become lower, and in this case, the pressure may be gradually lowered in the range of 0 barg to 0.5 barg described above. More specifically, the pressure at the latter stage may be controlled to start at 0.4 barg, go through 0.2 barg, and be down to atmospheric pressure. As such, when the pressure is controlled to be further lowered, there is an advantage in that the stability of the process may be promoted by lowering the pressure at the latter stage of reaction, which requires relatively less pressurization.

Meanwhile, according to an embodiment of the present invention, the raw materials input to the preparation of the ester-based composition is a polycarboxylic acid and a mono-alcohol as described above, and the reaction occurs theoretically in a molar ratio of 1 mol of carboxyl group to 1 mol of hydroxy group. More specifically, when the polycarboxylic acid is a dicarboxylic acid, the reaction between the dicarboxylic acid and the mono-alcohol occurs in a molar ratio of 1:2, and when the polycarboxylic acid is a tricarboxylic acid, the reaction between the tricarboxylic acid and the mono-alcohol occurs in a molar ratio of 1:3. Accordingly, the theoretical amount of carboxylic acid and mono-alcohol added as raw materials may be in a molar ratio of 1:2 to 1:8 with respect to divalent to tetravalent carboxylic acids.

This molar ratio is within the range that satisfies a minimum amount required for the reaction, and prevents energy loss due to unnecessary reflux caused by excessive alcohol input, and considering the excess amount of alcohol required in terms of achieving conversion rates of the reaction and controlling minimum residence time, the mono-alcohol may be added in an excess amount of 20 mol % to 100 mol % relative to the polycarboxylic acid equivalent. In the present invention, that the mono-alcohol is added in excess relative to the polycarboxylic acid equivalent indicates that greater than the amount of the mono-alcohol required to make the entire amount of the polycarboxylic acid react, that is an excess amount of mono-alcohol relative to the equivalent is added. More specifically, for example, that the mono-alcohol is added in more than 60 mol % relative to the polycarboxylic acid equivalent indicates that the mono-alcohol is added in 160 mol % of the equivalent. In the present invention, the amount of mono-alcohol added in excess may be 20 mol % or more, 30 mol % or more, 40 mol % or more, or 50 mol % or more, and may be 100 mol % or less, 90 mol % or less, 80 mol % or less, or 70 mol % or less relative to the polycarboxylic acid equivalent. When the excess amount of mono-alcohol is within the ranges described above, effects resulting from pressure control as described above may be maximized. Specifically, in applying the preparation method of the present invention, when the amount of mono-alcohol added in excess is 20 mol % to 40 mol % relative to the polycarboxylic acid equivalent, energy use may be improved to maximum, and when the amount thereof is 40 mol % to 100 mol %, productivity may also be further improved to maximum.

In addition, the mono-alcohol is input in excess, and thus, other than being input before the beginning of reaction, the mono-alcohol may be input also during the reaction. Therefore, the preparation method of the present invention may further include additionally inputting the mono-alcohol in the course of reactions (Sa). There is a benefit that when the mono-alcohol is not entirely input before the start of reaction but is input in portions in the course of the reaction at an appropriate time point, unnecessary energy use to heat the excess alcohol input at the beginning of reaction may be reduced. However, when the alcohol input is divided as such, the initial reaction rate may be lower than when the entire amount is added at the start of the reaction because the amount of the initial alcohol is relatively small compared to the case where the entire amount is added before the start of reaction. Therefore, additional input of mono-alcohol during the reaction and the amount thereof is preferable determined considering the balance between the reaction rate and the energy use.

When the mono-alcohol is additionally input during the reaction, the time point may be when the conversion rate reaches 20% or more or 30% or more, and 60% or less, or 50% or less. When the mono-alcohol is additionally input at an excessively early stage, the advantage of additional input of mono-alcohol as described above is not achievable, whereas when the mono-alcohol is additionally input at an excessively latter stage, the effect of improving the reaction rate according to the additional input of mono-alcohol may be insignificant because already little polycarboxylic acid remains.

When the pressure of reactors and optionally the excess input amount of alcohol are controlled as such, productivity may be increased due to improved reaction rate and reduced conversion time to reach a peak, energy use is minimized to promote process efficiency, and the pressure and the excess input amount of alcohol as described above may be each independently controlled in N batch reactors.

In the preparation method of the present invention, in the step S2, putting a reaction mixture into each reactor, raising temperature, performing a reaction, and discharging reaction products are carried out all at the same time, and thus, at least one of a plurality of reactors should receive the reaction mixture, at least another one of the plurality of reactors should perform the reaction, and at least the other one of the plurality of reactors should discharge the reaction products. Accordingly, N above is preferably an integer of 3 or more.

In particular, N above may be an integer of 3 to 10, an integer of 3 to 7, or an integer of 3 to 5. When there are too many reactors, a variety of additional equipment facilities are needed, including a supply controller for controlling a reaction mixture to be put into each reactor in order and reaction products to be discharged from each reactor. Furthermore, reaction duration per one reactor may be shorter than the sum of the input time of the raw materials put into a reactor and the discharge time of reaction products, so that there may be time during which the reactor does not operate before receiving raw materials, which may adversely affect productivity. In addition, the space required for the placement of each reactor becomes also excessive, which may be inefficient in terms of costs for the entire process.

In the step S2 of the preparation method of the present invention, an esterification reaction of a polycarboxylic acid and a mono-alcohol having 3 to 12 alkyl carbon atoms is performed. The esterification reaction refers to a reaction in which a hydroxyl group of an alcohol reacts with a carboxylic acid group of a polycarboxylic acid to form an ester bond, and the esterification reaction in the step S2 may occur at 120 to 250° C., preferably 140 to 230° C., more preferably 150 to 230° C. When the temperature raised in the step S2 is lower than the above ranges, the energy required for the reaction is not sufficiently supplied and thus the reaction may not sufficiently proceed, and when the temperature raised in the step S2 is higher than above ranges, as in the step S1, vaporization of the reaction mixture components may occur during the reaction, and thus a sufficient amount of the reaction product may not be generated.

Separation Step (S3)

The preparation method of the present invention also includes moving reaction products semi-continuously to a separation unit to remove unreacted alcohol (S3).

Specifically, the step S3 refers to a step in which reaction products produced in each of N batch reactors are semi-continuously moved to a separation unit, and then unreacted alcohol is removed from the separation unit. As described above, just as the input of the reaction mixture into the N batch reactors may be sequential, the discharge of the reaction products produced in each reactor may also be sequential or semi-continuous.

The separation unit used in the step S3 may include at least one separation column. Depending on the number of stages of the separation column included in the separation unit in the preparation method of the present invention, the composition ratio of a composition to be finally prepared may vary. Those skilled in the art may appropriately adjust the number of stages of the separation column included in the separation unit according to the composition ratio or properties of the composition to be prepared. In addition, the separation unit may include a purification tank of a drum type in addition to the separation column. The separation unit may remove the amount of unreacted alcohol included in the reaction products to a level of 30% or less, preferably 20% or less, more preferably 10% or less of the total. Since the unreacted alcohol is removed as described above, the physical properties of an ester-based composition to be prepared may be uniform and excellent.

Typically, continuous operation of the separation column is advantageous in terms of production management, and for this, reaction products discharged from each reactor may temporarily stay in a facility such as a tank before being put into the separation column. The reaction products including unreacted alcohol in the facility may be retained at a level of 0.1 to 10 hours, and there is no limitation on the size of the facility as long as the facility is in the size capable of stably and continuously supplying the reaction products to the separation column.

Catalyst Addition Step (S1-1, S1-1, S1-2, and/or S2a)

The preparation method of the present invention may further include at least one selected from the group consisting of: adding a catalyst to the reaction mixture between the step S1 and the step S2 (S1-1), adding a catalyst to a polycarboxylic acid or mono-alcohol before the step S1 (S1-2), and adding a catalyst to each of the N batch reactors of the step S2 (S2a).

The steps S1-1, S1-2, and S2a are preparation steps related to a catalyst addition, and may include putting a catalyst into a mixer, mixing the catalyst with reaction raw materials and inputting, or putting the catalyst into a batch reactor, and at least one step selected from among these may be performed to put the catalyst into a reaction system. The catalyst may be added in any step, but when added in the step S2a, there may be an advantage in preventing side reactions with the catalyst, and when directly added to raw alcohol, there may be an advantage in overall process efficiency. In addition, when the catalyst is added through the step S1-1 or the step S1-2 and further added in the step S2a, it is also possible to put the catalyst into the reactor during the reaction. When the catalyst is input as such, it may prevent reactivity deterioration caused when a portion of catalyst is deactivated during the reaction.

The catalyst used in the preparation method of the present invention may be at least one selected from an acid catalyst such as sulfuric acid, hydrochloric acid, phosphoric acid, nitric acid, para-toluenesulfonic acid, methanesulfonic acid, ethanesulfonic acid, propanesulfonic acid, butanesulfonic acid, alkyl sulfuric acid, metal salt such as aluminum lactate, lithium fluoride, potassium chloride, cesium chloride, calcium chloride, iron chloride, and aluminum phosphate, metal oxide such as heteropolyacid, natural/synthetic zeolite, cation and anion exchange resin, and organic metal such as tetraalkyl titanate and a polymer thereof, and may preferably be tetraalkyl titanate. Examples of the tetraalkyl titanate include TiPT, TnBT, TEHT, and the like. As such, it is preferable to use tetraalkyl titanate as a catalyst, because catalyst by-products that may be generated in subsequent processes are controlled or not generated.

The amount of catalyst to be used may vary depending on the type of catalyst, and for example, a homogeneous catalyst may be used in an amount of 0.01 to 5 parts by weight, 0.01 to 3 parts by weight, 0.1 to 1 parts by weight, 0.1 to 0.5 parts by weight, or 0.1 to 0.3 parts by weight with respect to 100 parts by weight of polycarboxylic acid, and a heterogeneous catalyst may be used in an amount of 5 to 200 parts by weight, 5 to 100 parts by weight, 20 to 200 parts by weight, or 20 to 150 parts by weight with respect to 100 parts by weight of polycarboxylic acid. When the amount of the catalyst used is too small, catalyst activity itself is small and the reaction may not proceed well, and when the amount of the catalyst used is too large, in addition to an increase in catalyst cost, an excessive catalyst rather causes a reverse reaction, which may lead to reduced final conversion rate.

Trans Reaction Step (S4)

The preparation method of the present invention may further include putting mono-alcohol having 3 to 12 alkyl carbon atoms into the reaction products from which the unreacted alcohol is removed to perform a trans-esterification reaction (S4), wherein the input alcohol in the step is different from the input alcohol in the step S1.

Through the step S4, it is possible to prepare a composition including two or more types of ester compounds. Those skilled in the art may select suitable alcohol according to the type of an ester compound to be included in the composition and perform a trans-esterification reaction. It is preferable that the step S4 is performed after the removal of unreacted alcohol. When the step S4 is performed before the removal of the unreacted alcohol, a trans-esterification reaction with newly added alcohol may not be easily performed due to the remaining unreacted alcohol, and even when the reaction is performed to a certain degree, the alcohol content is too high to deteriorate the efficiency of the reaction. Therefore, it is preferable that the amount of the unreacted alcohol included in the reaction products before the trans-esterification reaction is 10% or less.

EXAMPLES

Hereinafter, the present invention will be described in more detail with reference to Examples. However, the following Examples are for illustrative purposes only to describe the present invention and are not intended to limit the scope of the present invention.

Materials and Equipment

Phthalic acid was used as polycarboxylic acid, 2-ethylhexanol was used as mono-alcohol, and tetrabutyl titanate was used as a catalyst. As a preparation system for carrying out reactions, the preparation system shown in FIG. 1 of the present invention was used, and the number of batch reactors in the preparation system was set to three.

Examples and Comparative Examples

An esterification reaction of phthalic acid and 2-ethylhexanol was performed using the materials and equipment described above. In each Example and Comparative Example, applying pressure and/or pressure release were performed with respect to the same specific time point for three reactors, or control such as adding 2-ethylhexanol or a catalyst was performed, and according to controlled conditions, Examples and Comparative Examples were divided into groups and outlined below. Meanwhile, the amount of alcohol added in excess in this Example and Comparative Example is a value corresponding to the mole % of 2-ethylhexanol added in excess relative to the phthalic acid equivalent, and for example, when 320 mol of 2-ethylhexanol is added relative to 100 mol of phthalic acid, 120 mol of 2-ethylhexanol is further added relative to the equivalent of 200 mol. In this case, the amount of excess alcohol is 120/200*100 mol %=60 mol %. In addition, a catalyst was added in an amount of 0.23 wt % relative to the added phthalic acid. In addition, in this Example and Comparative Example, the pressure release time indicates the time taken from the initiation of reaction, and a blank area in the table indicates omission of measurement. In addition, temperature inside reactors and conversion rate measured for each Example and Comparative Example are values measured and calculated for any one of the three reactors.

Group 1. Confirmation of Effect of Applying Pressure and Pressure Release Control Phthalic acid, 2-ethylhexanol, and tetrabutyl titanate as a catalyst were put into a batch reactor, and an esterification reaction was performed by heating the batch reactor. In each case, adjusting the amount of excess alcohol, increasing initial reaction pressure, or adjusting pressure release time, and the like were performed, and specific conditions were outlined as follows.

TABLE 1

| | Excess input amount of alcohol (mol %) | Early stage pressure (barg) | Latter stage pressure (barg) | Pressure release time (min) |
|---|---|---|---|---|
| Comparative Examples 1-1 | 60 | Atmospheric pressure | Atmospheric pressure | — |

TABLE 1-continued

| | Excess input amount of alcohol (mol %) | Early stage pressure (barg) | Latter stage pressure (barg) | Pressure release time (min) |
|---|---|---|---|---|
| Comparative Examples 1-2 | 60 | 0.8 | 0.8 | — |
| Example 1-1 | 60 | 0.8 | 0.2 | 180 |
| Example 1-2 | 60 | 0.8 | Atmospheric pressure | 180 |
| Example 1-3 | 60 | 0.8 | Atmospheric pressure | 300 |
| Reference Example 1-1 | 0 | Atmospheric pressure | Atmospheric pressure | — |
| Reference Example 1-2 | 0 | 0.8 | 0.8 | — |

Table 2 shows the temperature inside the reactors over time in Comparative Examples, Examples, and Reference Examples of Table 1, and Table 3 shows conversion rates. Meanwhile, the conversion rates were calculated by measuring the cumulative generated water mass up to each time, and dividing the measured cumulative generated water mass by theoretical generated water mass generated when 100% conversion is achieved, and measurements and calculations were made from 120 minutes after the initiation of the reaction, which is the point at which the generated water was confirmed in earnest.

TABLE 2

| | Temperature inside reactor (° C.) | | | | | | |
|---|---|---|---|---|---|---|---|
| Time (min) | Comparative Examples 1-1 | Comparative Examples 1-2 | Example 1-1 | Example 1-2 | Example 1-3 | Reference Example 1-1 | Reference Example 1-2 |
| 10 | 43 | 42 | 42 | 44 | 43 | 45 | 39 |
| 20 | 64 | 62 | 62 | 64 | 63 | 69 | 63 |
| 30 | 78 | 77 | 77 | 77 | 78 | 83 | 80 |
| 40 | 100 | 100 | 99 | 99 | 99 | 107 | 107 |
| 50 | 121 | 121 | 120 | 120 | 120 | 128 | 128 |
| 60 | 135 | 135 | 135 | 135 | 133 | 146 | 145 |
| 70 | 157 | 155 | 157 | 157 | 154 | 172 | 172 |
| 80 | 176 | 178 | 179 | 178 | 177 | 177 | 186 |
| 90 | 179 | 190 | 187 | 189 | 187 | 182 | 196 |
| 100 | 183 | 198 | 196 | 198 | 196 | 183 | 203 |
| 110 | 184 | 204 | 204 | 204 | 203 | 183 | 204 |
| 120 | 185 | 205 | 205 | 205 | 202 | 184 | 204 |
| 150 | 186 | 210 | 208 | 208 | 208 | 187 | 211 |
| 180 | 189 | 215 | 204 (Pressure reduction) | 203 (Pressure reduction) | 213 | 190 | 216 |
| 210 | 190 | 217 | 204 | 199 | 217 | 195 | 220 |
| 240 | 194 | 222 | 204 | 200 | 221 | 200 | 224 |
| 270 | 197 | 224 | 208 | 203 | 224 | 206 | 228 |
| 300 | 199 | 228 | 210 | 204 | 227 (Pressure reduction) | 214 | 231 |
| 330 | 206 | 232 | 215 | 206 | 210 | 221 | 234 |
| 360 | 212 | 234 | 219 | 208 | 209 | 228 | — |
| 380 | — | | 222 | 211 | — | — | — |
| 390 | — | 237 | — | 211 | 209 | — | — |
| 410 | — | 237 | — | — | — | — | — |
| 430 | — | — | — | — | 211 | — | — |

TABLE 3

| | Conversion rate (%) | | | | | | |
|---|---|---|---|---|---|---|---|
| Time (min) | Comparative Examples 1-1 | Comparative Examples 1-2 | Example 1-1 | Example 1-2 | Example 1-3 | Reference Examples 1-1 | Reference Examples 1-2 |
| 120 | 12.42 | 17.04 | 17.04 | 17.39 | 13.84 | 13.13 | 14.20 |
| 150 | 21.65 | 36.92 | 35.50 | 35.85 | 31.24 | 23.43 | 25.56 |
| 180 | 34.08 | 52.18 | 50.05 (Pressure reduction) | 50.76 (Pressure reduction) | 47.21 | 33.72 | 37.27 |
| 210 | 45.44 | 62.12 | 60.35 | 60.70 | 59.64 | 44.04 | 40.82 |
| 240 | 56.44 | 70.64 | 69.93 | 71.35 | 68.87 | 52.89 | 45.79 |
| 270 | 68.87 | 79.16 | 78.10 | 77.03 | 77.03 | 59.28 | 51.12 |
| 300 | 80.58 | 85.55 | 86.61 | 83.42 | 82.71 (Pressure reduction) | 68.16 | 53.60 |
| 330 | 93.36 | 91.23 | 93.00 | 88.74 | 89.10 | 74.55 | 56.80 |
| 360 | 98.33 | 95.13 | 97.62 | 94.42 | 92.29 | 76.68 | 56.80 |
| 380 | — | — | 98.68 | 96.55 | — | 76.68 | 56.80 |
| 390 | — | 97.62 | — | 97.62 | 96.55 | — | — |
| 410 | — | 99.04 | — | | — | — | — |
| 430 | — | — | — | | 98.33 | — | — |

As shown in Tables 2 and 3 above, it is confirmed that in Examples 1-1 and 1-2 in which the reaction was initiated under pressure, but the pressure was released or reduced at the time of about 50% conversion, a high conversion rate was achieved at a faster time than in Comparative Examples and Reference Examples, and the temperature inside the reactor at the time when the final conversion was achieved was also in the ideal temperature range of 210 to 230° C., thereby minimizing energy loss during the reaction.

On the other hand, in Comparative Example 1-1 in which no pressure was applied, as a large amount of alcohol was vaporized during the reaction, the conversion rate increased slowly compared to Example, and the final conversion rate also showed a lower value than in Example. This indicates that a significant portion of the vaporized alcohol was not involved in the reaction again, resulting in loss of raw materials, and thus, a desired ester-based compound is not sufficiently prepared. In addition, in Comparative Example 1-2 in which pressure was applied and maintained until the end of reaction without pressure reduction during the reaction, as the vaporized alcohol was pressurized to be involved in the reaction again after liquefaction, the conversion rate increased faster than in Comparative Example 1-1, but the temperature inside the reactor became higher than the preferred range as the amount of liquefied alcohol remained relatively high even after the middle of the reaction in which phthalic acid was consumed to some extent. This may contribute to deterioration of product quality obtained when the final conversion rate is achieved.

In addition, it was confirmed that in Reference Examples 1-1 and 1-2 in which the alcohol was not input in excess, but was input according to the equivalent, and pressure reduction was not performed after pressurization, a large amount of alcohol vaporization occurred during the reaction, resulting in insufficient amount of alcohol to be involved in the reaction, and thus, the conversion rate did not increase above a certain value and stayed still. This means that the desired reaction was not sufficiently achieved, indicating that, in the esterification reaction carried out in the present invention, an excess of alcohol needs to be input to achieve a sufficient conversion rate.

Group 2. Confirmation of Effect According to Catalyst Input/Split Input

It was performed in the same manner as in Example of Group 1, except that when the amount of catalyst (0.23 wt % relative to phthalic acid) initially input in Example of Group 1 is 100%, in addition to the catalyst input of 100%, the catalyst was additionally input thereafter, or the 100% catalyst input was divided. Specific conditions for each case are outlined in Table 4 below.

TABLE 4

| | Excess input amount of alcohol (mol %) | Early stage pressure (barg) | Latter stage pressure (barg) | Pressure release time (min) | Initial catalyst Input (%) | Additional catalyst input (%)/Time (min) |
|---|---|---|---|---|---|---|
| Example 2-1 | 60 | 0.8 | Atmospheric pressure | 150 | 100 | 100%/180 min |
| Example 2-2 | 60 | 0.8 | Atmospheric pressure | 150 | 100 | 1) 100%/120 min<br>2) 100%/240 min |
| Example 2-3 | 40 | 0.8 | Atmospheric pressure | 270 | 100 | 100%/300 min |
| Example 2-4 | 40 | 0.8 | Atmospheric pressure | 270 | 50 | 50%/270 min |

In addition, in the same manner as in Group 1 above, the temperatures inside the reactors and conversion rates over time in Examples of Table 4 above are outlined in Table 5.

TABLE 5

| | Example 2-1 | | Example 2-2 | | Example 2-3 | | Example 2-4 | |
|---|---|---|---|---|---|---|---|---|
| Time (min) | Temperature (° C.) | Conversion rate (%) | Temperature (° C.) | Conversion rate (%) | Temperature (° C.) | Conversion rate (%) | Temperature (° C.) | Conversion rate (%) |
| 10 | 42 | | 45 | | 44 | | 41 | |
| 20 | 63 | | 62 | | 65 | | 64 | |
| 30 | 77 | | 77 | | 80 | | 79 | |
| 40 | 100 | | 99 | | 106 | | 102 | |
| 50 | 121 | | 135 | | 125 | | 124 | |
| 60 | 134 | | 157 | | 140 | | 137 | |
| 70 | 158 | | 178 | | 166 | | 157 | |
| 80 | 179 | | 183 | | 185 | | 178 | |
| 90 | 189 | | 189 | | 195 | | 197 | |
| 100 | 198 | | 197 | | 202 | | 201 | |
| 110 | 204 | | 204 | | 204 | | 201 | |
| 120 | 204 | 14.91 | 204 | 16.33 | 205 | 20.59 | 204 | 15.97 |
| 150 | 207 (Pressure reduction) | 31.24 | 210 (Pressure reduction) | 38.34 | 211 | 36.21 | 206 | 30.88 |
| 180 | 194 | 41.53 | 215 | 52.18 | 217 | 48.99 | 210 | 45.08 |
| 210 | 193 | 56.09 | 219 | 60.35 | 219 | 58.57 | 214 | 59.64 |
| 240 | 194 | 67.80 | 222 | 68.87 | 223 | 67.09 | 220 | 74.19 |
| 270 | 199 | 77.74 | 225 | 79.52 | 227 (Pressure reduction) | 72.77 | 226 (Pressure reduction) | 78.81 |
| 300 | 203 | 86.61 | 227 | 84.13 | 205 | 82.00 | 207 | 85.19 |
| 330 | 207 | 94.42 | | | 211 | 89.45 | 211 | 94.07 |
| 335 | | | 230 | 90.87 | | | | |
| 340 | 208 | 97.26 | | | | | | |
| 360 | 211 | 99.99 | 232 | 95.13 | 215 | 94.78 | 218 | 98.68 |
| 380 | | | | | 218 | 97.62 | | |
| 390 | | | 236 | 97.62 | | | | |
| 400 | | | | | 220 | 99.04 | | |
| 410 | | | | | — | 99.39 | | |

As seen in Table 5, Examples 2-1 to 2-3 in which the catalyst was additionally input, all showed high final conversion rates. In addition, when comparing Examples 2-1 and 2-2 in which 100% of the catalyst was input or 200% of the catalyst was input in the same conditions, in Example 2-1, in which 100% of the catalyst was input only once at 180 minutes, a high conversion rate was achieved in a faster time, whereas in Example 2-2 in which 100% of the catalyst was additionally input at 120 minutes and 240 minutes each, the reaction more than necessary was activated according to the excess catalyst, which led to an increase in temperature inside the reactor to probably cause the conversion rate to increase rather later than in Example 2-1. In addition, when comparing Example 2-3 in which the pressure was reduced at the same time point, but the catalyst was additionally input with Example 2-4 in which the catalyst input was divided, it was confirmed that the temperature inside the reactor increased similarly, but the final conversion rate was higher in Example 2-3 with greater catalyst input. This suggests that an increase in catalyst input may lead to an improvement in conversion rate. However, as seen from the comparison of Examples 2-1 and 2-2 described above, an excessive increase in the input amount of catalyst may have a rather adverse effect, and thus, the amount of catalyst input may need to be determined within an appropriate range.

Group 3. Confirmation of Effect According to the Input Amount of Alcohol

It was performed in the same manner as in Example of Group 1, except that the amount of excess alcohol was adjusted, and a catalyst corresponding to 100% was additionally input during the reaction. Specific conditions for each case are outlined in Table 6 below.

TABLE 6

| | Excess input amount of alcohol (mol %) | Early stage pressure (barg) | Latter stage pressure (barg) | Pressure release time (min.) | Additional input time of catalyst (min.) |
|---|---|---|---|---|---|
| Example 3-1 | 60 | 0.8 | Atmospheric pressure | 270 | 300 |
| Example 3-2 | 50 | 0.8 | Atmospheric pressure | 270 | 300 |
| Example 3-3 | 40 | 0.8 | Atmospheric pressure | 270 | 300 |
| Example 3-4 | 60 | 0.6 | Atmospheric pressure | 270 | 270 |
| Example 3-5 | 40 | 0.6 | Atmospheric pressure | 270 | 270 |

In addition, in the same manner as in Group 1 above, the temperatures inside the reactors and conversion rates over time in Examples of Table 6 above are outlined in Table 7.

TABLE 7

| | Example 3-1 | | Example 3-2 | | Example 3-3 | | Example 3-4 | | Example 3-5 | |
|---|---|---|---|---|---|---|---|---|---|---|
| Time (min) | Temperature (° C.) | Conversion rate (%) | Temperature (° C.) | Conversion rate (%) | Temperature (° C.) | Conversion rate (%) | Temperature (° C.) | Conversion rate (%) | Temperature (° C.) | Conversion rate (%) |
| 10 | 45 | | 36 | | 44 | | 35 | | 41 | |
| 20 | 62 | | 58 | | 65 | | 57 | | 64 | |
| 30 | 77 | | 76 | | 80 | | 73 | | 79 | |
| 40 | 99 | | 104 | | 106 | | 94 | | 103 | |
| 50 | 121 | | 124 | | 125 | | 117 | | 124 | |
| 60 | 135 | | 139 | | 140 | | 133 | | 137 | |
| 70 | 156 | | 163 | | 166 | | 152 | | 164 | |
| 80 | 178 | | 180 | | 185 | | 176 | | 181 | |
| 90 | 190 | | 194 | | 195 | | 187 | | 191 | |
| 100 | 197 | | 201 | | 202 | | 195 | | 198 | |
| 110 | 203 | | 203 | | 204 | | 198 | | 202 | |
| 120 | 202 | 18.46 | 205 | 21.65 | 205 | 20.59 | 200 | 17.75 | 202 | 19.52 |
| 150 | 209 | 36.56 | 211 | 39.40 | 211 | 36.21 | 203 | 36.56 | 205 | 36.92 |
| 180 | 213 | 52.18 | 217 | 53.46 | 217 | 48.99 | 209 | 53.60 | 210 | 51.83 |
| 210 | 218 | 63.90 | 220 | 62.83 | 219 | 58.57 | 214 | 68.87 | 216 | 62.83 |
| 240 | 222 | 73.48 | 224 | 71.71 | 223 | 67.09 | 219 | 75.97 | 220 | 71.35 |
| 270 | 219 (Pressure reduction) | 81.29 | 228 (Pressure reduction) | 77.03 | 227 (Pressure reduction) | 72.77 | 223 (Pressure reduction) | 83.77 | 225 (Pressure reduction) | 77.39 |
| 300 | 205 | 90.52 | 206 | 84.84 | 205 | 82.00 | 205 | 91.94 | 209 | 85.19 |
| 330 | 209 | 97.26 | 210 | 93.36 | 211 | 89.45 | 211 | 97.26 | 214 | 93.36 |
| 340 | 211 | 98.33 | | | | | | | | |
| 350 | | | 213 | 96.55 | | | | | | |
| 360 | | | | | 215 | 94.78 | | | 219 | 97.97 |
| 370 | | | 216 | 99.04 | | | | | | |
| 380 | | | | | 218 | 97.62 | | | 223 | 99.39 |
| 400 | | | | | 220 | 99.04 | | | | |
| 410 | | | | | — | 99.39 | | | | |

As shown in Table 7, it was confirmed that when only the input amount of alcohol is adjusted in the same conditions, greater alcohol input leads to greater amount of alcohol involved in the reaction, thereby resulting in a rapid increase in conversion rate. However, greater alcohol input requires greater energy use for heating the excess alcohol. Therefore, it is preferable to determine an appropriate input amount of alcohol within the scope of the present invention considering target reaction completion time, energy use, and the like.

Group 4. Confirmation of Effect According to Additional Input of Alcohol and Catalyst It was performed in the same manner as in Example of Group 1, except that a portion of excess alcohol was input during the reaction, and a catalyst was also additionally input during the reaction. Specific conditions for each case are outlined in Table 8 below.

TABLE 8

| | Excess input amount of alcohol (Initial input/Intermediate input, mol %) | | Intermediate input time of alcohol (min) | Early stage pressure (barg) | Latter stage pressure (barg) | Pressure release time (min) | Additional input of catalyst (%) | Additional input time of catalyst (min.) |
|---|---|---|---|---|---|---|---|---|
| Example 4-1 | 20 | 20 | 180 | 0.8 | Atmospheric pressure | 270 | 100 | 270 |
| Example 4-2 | 20 | 20 | 180 | 0.5 | Atmospheric pressure | 270 | 100 | 270 |

In addition, in the same manner as in Group 1 above, the temperatures inside the reactors and conversion rates over time in Examples of Table 8 are outlined in Table 9.

TABLE 9

| | Example 4-1 | | Example 4-2 | |
|---|---|---|---|---|
| Time (min) | Temperature (° C.) | Conversion rate (%) | Temperature (° C.) | Conversion rate (%) |
| 10 | 46 | | 43 | |
| 20 | 66 | | 66 | |
| 30 | 80 | | 82 | |
| 40 | 102 | | 102 | |
| 50 | 125 | | 125 | |
| 60 | 138 | | 138 | |
| 70 | 162 | | 159 | |
| 80 | 180 | | 179 | |

TABLE 9-continued

| | Example 4-1 | | Example 4-2 | |
|---|---|---|---|---|
| Time (min) | Temperature (° C.) | Conversion rate (%) | Temperature (° C.) | Conversion rate (%) |
| 90 | 193 | | 189 | |
| 100 | 201 | | 197 | |
| 110 | 205 | | 195 | |
| 120 | 205 | 13.13 | 197 | 12.07 |
| 150 | 210 | 28.40 | 202 | 24.85 |
| 180 | 215 | 39.76 | 206 | 38.69 |
| 210 | 217 | 50.05 | 214 | 48.28 |
| 240 | 220 | 58.57 | 219 | 57.86 |
| 270 | 225 (Pressure reduction) | 65.67 | 222 (Pressure reduction) | 65.32 |
| 300 | 202 | 74.19 | 202 | 74.55 |
| 330 | 206 | 83.07 | 206 | 83.42 |
| 360 | 211 | 89.81 | 211 | 89.81 |
| 390 | 216 | 94.78 | 215 | 95.49 |
| 420 | 219 | 98.33 | 219 | 97.62 |
| 430 | 220 | 99.39 | | |

As shown in Table 9, It was confirmed that even when the excess alcohol was not input all at once before the initiation of reaction, but was input during the reaction, using the preparation method of the present invention, which applies pressure at the initiation of reaction and releases pressure during the reaction, a desired ester-based material was possibly prepared at a high conversion rate.

Group 5. Confirmation of Effect According to Additional Control of Latter Stage Pressure It was performed in the same manner as in Example of Group 1, except that after performing pressure reduction from early stage pressure to latter stage pressure, the latter stage pressure was further reduced. Specific conditions for each case are outlined in Table 10 below.

TABLE 10

| | Excess input amount of alcohol (mol %) | Early stage pressure (barg) | Latter stage pressure and time of change (barg/min) | | | Initial input of catalyst (%) | Additional input of catalyst (%) | Intermediate input time of alcohol (min) |
|---|---|---|---|---|---|---|---|---|
| Example 5-1 | 40 | 0.5 | 0.4 (270) | 0.2 (330) | Atmospheric pressure (390) | 100 | 100 | 270 |

Specifically, in Example 5-1, the pressure was lowered from 0.8 barg to 0.4 barg at 270 minutes, then the pressure was further lowered to 0.2 barg at 330 minutes, and the pressure was lowered to atmospheric pressure at 390 minutes. In addition, in Example 5-1, 100% of the 200% catalyst was added at the initiation of reaction, and the remaining 100% was added at 270 minutes after the initiation of reaction.

In addition, in the same manner as in Group 1 above, the temperatures inside the reactors and conversion rates over time in Examples of Table 10 are outlined in Table 11.

TABLE 11

| | Example 5-1 | |
|---|---|---|
| Time (min) | Temperature (° C.) | Conversion rate (%) |
| 10 | 41 | |
| 20 | 63 | |
| 30 | 79 | |
| 40 | 102 | |
| 50 | 124 | |
| 60 | 135 | |
| 70 | 159 | |
| 80 | 180 | |
| 90 | 195 | |
| 100 | 202 | |
| 110 | 205 | |
| 120 | 204 | 16.33 |
| 150 | 208 | 32.30 |
| 180 | 214 | 45.44 |
| 210 | 219 | 56.44 |
| 240 | 223 | 63.54 |
| 270 | 226 (Pressure reduction) | 71.35 |
| 300 | 221 | 77.74 |
| 330 | 225 | 83.77 |
| 360 | 220 | 88.39 |
| 390 | 223 | 91.94 |
| 420 | 217 | 94.78 |
| 450 | 219 | 95.49 |

As shown in Table 11, it was confirmed that even when the pressure at the latter stage of reaction was controlled in such a way that the pressure at the latter stage of reaction was not lowered all at once but was lowered slowly, a high conversion rate was achieved similarly to the case in which the pressure at the latter stage of reaction was lowered all at once. In addition, when the pressure is gradually changed as such, there is an advantage in that the stability of the process may be obtained compared to when the pressure is changed at once.

DESCRIPTION OF SYMBOLS

1: Mixer

11: Input path of polycarboxylic acid

12: Input path of alcohol

13: Input path of catalyst

2: Supply controller

3: Reaction unit

31 to 3N: Each batch reactor (a total of N)

4: Separation unit

41: Movement path of ester-based composition from which unreacted alcohol is removed

42: Movement path of removed unreacted alcohol

5: Trans reaction unit

51: Input path of alcohol different from alcohol put into 12

52: Movement path of ester-based composition subjected to trans-esterification reaction

The invention claimed is:

1. A method for preparing an ester-based composition, comprising:

putting a polycarboxylic acid and a mono-alcohol having 3 to 12 alkyl carbon atoms into a mixer to form a reaction mixture (step S1);

sequentially putting the reaction mixture into each of N batch reactors connected in parallel to perform a reaction, and sequentially completing the reaction in the N batch reactors to semi-continuously produce reaction products (step S2); and semi-continuously moving the reaction products to a separation unit to remove unreacted alcohol (step S3), wherein N is an integer of 3 or more, pressures of the N batch reactors are each independently configured such that pressure at an early stage is 0.3 barg to 1.0 barg and pressure at a latter stage is 0 barg to 0.5 barg, the pressure at the early stage is greater than the pressure at the latter stage, and the early and latter stages are divided based on any one of the time points when reaction conversion rate is 30% to 90%.

2. The method of claim 1, wherein the batch reactors have the pressure at the early stage of 0.4 barg to 1.0 barg, and the pressure at the latter stage of 0 barg to 0.4 barg.

3. The method of claim 1, wherein the mono-alcohol is added in excess of 20 mol % to 100 mol % relative to polycarboxylic acid equivalent.

4. The method of claim 1, wherein the pressure at the latter stage gradually decreases as reactions proceed.

5. The method of claim 1, further comprising additionally inputting the mono-alcohol in a course of reactions.

6. The method of claim 1, further comprising at least one selected from the group consisting of:

adding a catalyst to the reaction mixture between the step S1 and the step S2;

adding the catalyst to a polycarboxylic acid and mono-alcohol before the step S1; and adding the catalyst to each of the N batch reactors of the step S2.

7. The method of claim 6, wherein the catalyst comprises tetraalkyl titanate.

8. The method of claim 1, wherein the step S1 further comprises heating the reaction mixture at 50 to 200° C.

9. The method of claim 1, wherein the reaction of the step S2 is performed at 130 to 250° C.

10. The method of claim 1, wherein the polycarboxylic acid is at least one selected from the group consisting of a dicarboxylic acid, a tricarboxylic acid, and a tetracarboxylic acid.

11. The method of claim 10, wherein the dicarboxylic acid is at least one selected from the group consisting of a linear dicarboxylic acid having 2 to 10 carbon atoms, a terephthalic acid, a phthalic anhydride, an isophthalic acid, a cyclohexane dicarboxylic acid, an anhydride thereof, and a derivative thereof;

the tricarboxylic acid is at least one selected from the group consisting of a citric acid, a trimellitic acid, a cyclohexane tricarboxylic acid, an anhydride thereof, and a derivative thereof; and the tetracarboxylic acid is at least one selected from the group consisting of a benzenetetracarboxylic acid, a furantetracarboxylic acid, a cyclohexane tetracarboxylic acid, a tetrahydrofuran tetracarboxylic acid, an anhydride thereof, and a derivative thereof.

* * * * *